US005855743A

United States Patent [19]
Herbst et al.

[11] Patent Number: 5,855,743
[45] Date of Patent: Jan. 5, 1999

[54] PROCESS OF ISOLATION OF (METH) ACRYLIC ACID

[75] Inventors: Holger Herbst, Frankenthal; Ulrich Hammon, Mannheim, both of Germany

[73] Assignee: BASF Aktiengesellschaft, Ludwigshafen, Germany

[21] Appl. No.: 902,291

[22] Filed: Jul. 29, 1997

Related U.S. Application Data

[63] Continuation of Ser. No. 587,473, Jan. 17, 1996, abandoned.

[30] Foreign Application Priority Data

Jan. 18, 1995 [DE] Germany ................. 195 01 326.3

[51] Int. Cl.$^6$ ................. B01D 3/00; C07C 51/44
[52] U.S. Cl. ................. 203/74; 203/80; 203/100; 203/DIG. 9; 203/DIG. 21; 562/600
[58] Field of Search ................. 203/DIG. 9, 74, 203/73, 80, DIG. 21, 100; 562/600

[56] References Cited

U.S. PATENT DOCUMENTS

| | | | |
|---|---|---|---|
| 2,147,306 | 2/1939 | McCulloch | 203/82 |
| 2,701,233 | 2/1955 | Quinn | 203/60 |
| 3,884,948 | 5/1975 | Gankin et al. | 562/600 |
| 3,893,895 | 7/1975 | Dehnert et al. | 203/38 |
| 4,199,410 | 4/1980 | Ohrui et al. | 203/DIG. 21 |
| 4,308,107 | 12/1981 | Markfort | 203/25 |
| 4,358,347 | 11/1982 | Mettetal et al. | 203/DIG. 21 |
| 4,464,229 | 8/1984 | Sato et al. | 203/DIG. 21 |
| 4,576,683 | 3/1986 | Cohen | 203/38 |
| 5,130,465 | 7/1992 | Ko Vasy et al. | 560/75 |
| 5,482,597 | 1/1996 | Herbst et al. | 203/DIG. 21 |
| 5,637,222 | 6/1997 | Herbst et al. | 210/634 |

FOREIGN PATENT DOCUMENTS

| | | |
|---|---|---|
| 0 092097 | 10/1983 | European Pat. Off. . |
| 0 102642 | 3/1984 | European Pat. Off. . |
| 0 117146 | 8/1984 | European Pat. Off. . |
| 0 253409 | 1/1988 | European Pat. Off. . |
| 0 297445 | 1/1989 | European Pat. Off. . |
| 2 136 396 | 2/1973 | Germany . |
| 22 07 184 | 8/1973 | Germany . |
| 43 08 087 | 9/1994 | Germany . |
| 44 31 949 | 3/1995 | Germany . |
| 44 31 957 | 3/1995 | Germany . |
| 44 05 059 | 8/1995 | Germany . |
| 1 346737 | 2/1974 | United Kingdom . |

*Primary Examiner*—Virginia Manoharan
*Attorney, Agent, or Firm*—Oblon, Spivak, McClelland, Maier & Neustadt, P. C.

[57] ABSTRACT

A process is provided for the isolation of (meth)acrylic acid from a mixture containing (meth)acrylic acid as the main component and lower aldehydes as secondary components by rectification in a rectification column having a stripping section and a rectification section, wherein the starting mixture containing the (meth)acrylic acid to be isolated by rectification is not fed directly to the rectification column but is first passed into a heated dwell vessel which is connected to the vapor side of the rectification section of the rectification column and in which the starting mixture is kept at the boil and, instead of the starting mixture as such, the bottom liquid of the dwell vessel is fed to the rectification column.

7 Claims, No Drawings

PROCESS OF ISOLATION OF (METH) ACRYLIC ACID

This application is a Continuation of application Ser. No. 08/587,473, filed on Jan. 17, 1996, now abandoned.

Isolation of (meth)acrylic acid from a mixture containing (meth)acrylic acid as the main component and lower aldehydes as secondary components by rectification in a rectification column consisting of a stripping section and a rectification section

FIELD OF THE INVENTION

The present invention relates to a novel process for the isolation of (meth)acrylic acid from a mixture containing (meth)acrylic acid as the main component and lower aldehydes as secondary components by rectification in a rectification column consisting of a stripping section and a rectification section.

DISCUSSION OF THE BACKGROUND (Meth)acrylic acid is used as an abbreviation and represents acrylic acid or methacrylic acid. (Meth)acrylic acid, either as such or in the form of its esters, is particularly important for the preparation of polymers for various applications, for example for use as adhesives.

(Meth)acrylic acid is obtainable, inter alia, by catalytic gas-phase oxidation of alkanes, alkanols, alkenes or alkenals of 3 or 4 carbon atoms. (Meth)acrylic acid is particularly advantageously obtainable, for example, by catalytic gas-phase oxidation of propene, acrolein, tert-butanol, isobutene, isobutane, isobutyraldehyde or methacrolein.

However, other possible starting compounds are those from which the actual $C_3/C_4$ starting compound is first formed as an intermediate during the gas-phase oxidation. An example is the methyl ether of tert-butanol.

These starting gases, as a rule diluted with inert gases, such as nitrogen, $CO_2$, saturated hydrocarbons and/or steam, are passed as a mixture with oxygen, at elevated temperatures (usually from 200° to 400° C.) and, if required, superatmospheric pressure, over transition metal mixed oxide catalysts (containing, for example, Mo, V, W and/or Fe) and are converted by oxidation into (meth)acrylic acid (cf. for example DE-A 4 405 059, EP-A 253 409, EP-A 92 097, DE-A 44 31 957 and DE-A 44 31 949).

Owing to the many parallel and secondary reactions taking place in the course of the catalytic gas phase oxidation and due to the inert dilution gases to be used concomitantly, the product of the catalytic gas-phase oxidation is, however, not pure (meth)acrylic acid but a reaction gas mixture which contains essentially (meth)acrylic acid, the inert dilution gases and byproducts, from which the (meth)acrylic acid must be separated. In addition to byproducts which are comparatively simple to remove from (meth)acrylic acid and are less troublesome in subsequent applications of the (meth)acrylic acid, for example acetic acid, the reaction gas mixture also contains in particular lower aldehydes, such as formaldehyde, acetaldehyde, acrolein, methacrolein, propionaldehyde, n-butyraldehyde, benzaldehyde, furfural and crotonaldehyde, which are related to (meth)acrylic acid and therefore more difficult to separate from (meth)acrylic acid, and in addition may contain maleic anhydride (the total amount of these secondary components, which frequently present considerable problems during subsequent applications, is as a rule $\leq 2\%$ by weight, based on the amount of (meth)acrylic acid contained in the reaction gas mixture).

The (meth)acrylic acid is usually isolated from the reaction mixture by extraction and rectification processes, ie. as a rule the (meth)acrylic acid formed is initially taken up from the reaction gas mixture of the gas-phase oxidation into a suitable absorbent. By separation of the absorbate by rectification, a crude (meth)acrylic acid is then usually obtained, from which a pure (meth)acrylic acid is frequently produced by passing through further separation stages involving rectification. The crude (meth)acrylic acid has, as a rule, a purity of >98% by weight, the impurities being in particular lower aldehydes and possibly maleic anhydride, whereas the separation of the (meth)acrylic acid from the absorption liquid takes place essentially quantitatively. In contrast to crude (meth)acrylic acid, the purity of the pure (meth)acrylic acid is usually >99% by weight.

DE-A 44 36 243 relates, for example, to a process for the isolation of (meth)acrylic acid from the reaction gas mixture of the catalytic gas-phase oxidation by countercurrent absorption with a high-boiling inert hydrophobic organic liquid, in which the reaction gas mixture is passed countercurrent to the descending high-boiling inert hydrophobic organic liquid in an absorption column, a rectification process is superposed on the absorption process taking place in the absorption column in a natural manner by withdrawing from the absorption column an amount of energy over and above its natural energy release taking place as a result of contact with the ambient temperature, and crude (meth) acrylic acid is isolated via the top by rectification from the liquid discharge of the absorption column (absorbate), which discharge contains (meth)acrylic acid and the absorbent as main components and lower aldehydes and possibly maleic anhydride as secondary components. DE-A 44 36 243 defines high-boiling inert hydrophobic organic liquids (absorbents) generally as those liquids whose boiling point at atmospheric pressure (1 atm) is above the boiling point of (meth)acrylic acid and which comprise at least 70% by weight of molecules which do not contain any externally acting polar group and are thus, for example, incapable of forming hydrogen bridges.

German Patent 2,136,396 and DE-A 43 08 087 likewise disclose the isolation of acrylic acid from the reaction gas mixture of the catalytic gas-phase oxidation of propylene and/or acrolein by countercurrent absorption with a high-boiling inert hydrophobic organic liquid. The process is essentially carried out by a method in which the reaction gas mixture is passed countercurrent to the descending absorption liquid in a conventional absorption column, the readily volatile secondary components which are easy to separate off are substantially removed, by stripping with inert gas in a desorption column, from the liquid discharge of the absorption column, which discharge is composed essentially of acrylic acid, the absorbent and secondary components, and the liquid discharge of the desorption column, which discharge contains acrylic acid and the absorbent as main components and lower aldehydes and possibly maleic anhydride as secondary components, is subsequently rectified in a rectification column in order to isolate crude acrylic acid via the top.

EP-A 297 445 relates, for example, to a process for the isolation of methacrylic acid from the reaction gas mixture of the catalytic gas-phase oxidation by absorption of the methacrylic acid in an absorption column operated with water. For isolation of crude methacrylic acid as a bottom product, the liquid discharge of the absorption column is rectified.

EP-A 117 146 relates to a process for the isolation of acrylic acid from the reaction gas mixture of the catalytic gas-phase oxidation by absorption of the acrylic acid in an absorption column operated with water. The acrylic acid is separated off from the liquid discharge by extraction with ethyl acetate and crude acrylic acid is obtained from the extract as a bottom product by rectification.

EP-B 102 642, British Patent 1,346,737 and DE-B 2 207 184 relate to the isolation of pure (meth)acrylic acid from crude (meth)acrylic acid by rectification. In order to increase the separation efficiency with respect to lower aldehydic impurities, it is advisable to add chemical compounds, such as primary amines, which bind the aldehydic impurities.

The abovementioned isolations of (meth)acrylic acid from a mixture containing (meth)acrylic acid as the main component and lower aldehydes as secondary components by rectification in a rectification column consisting of a stripping section and a rectification section are merely a small selection from the variety of such separation problems mentioned in the prior art.

A disadvantage of all these prior art separation processes by rectification, regardless of whether the (meth)acrylic acid is isolated via the top or via the bottom, is that the rectification apparatuses (in particular the evaporator surface) relatively rapidly become covered with a coating during the isolation by rectification, even when polymerization inhibitors, such as air, hydroquinone, hydroquinone monomethyl ether, para-nitrosophenol, para-methoxyphenol and/or phenothiazine, are present, and the rectification, which is usually carried out continuously, therefore has to be stopped from time to time in order to remove the coatings formed. The different colors of the coatings formed (black and white) show that at least two processes are involved in the formation of the coatings.

SUMMARY OF THE INVENTION

It is an object of the present invention to provide a novel process for the isolation of (meth)acrylic acid from a mixture containing (meth)acrylic acid as the main component and lower aldehydes as secondary components by rectification in a rectification column consisting of a stripping section and a rectification section, in which process the formation of coatings on the rectification apparatuses (in particular on the evaporator surface) is reduced.

We have found that this object is achieved by a process for the isolation of (meth)acrylic acid from a mixture containing (meth)acrylic acid as the main component and lower aldehydes as secondary components by rectification in a rectification column consisting of a stripping section and a rectification section, wherein the starting mixture comprising the (meth)acrylic acid to be isolated by rectification is not fed directly to the rectification column but is first passed into a heated dwell vessel which is connected to the vapor side of the rectification section of the rectification column and in which the starting mixture is kept at the boil and, instead of the starting mixture as such, the bottom liquid of the dwell vessel is fed to the rectification column (that part of the rectification column which is located below the entry point of the bottom liquid of the dwell vessel forms the stripping section of said column in the usual manner, and that part of the rectification column which is located above this entry point forms the rectification section of said column in the usual manner).

DETAILED DESCRIPTION OF THE PREFERRED EMBODIMENTS

In the novel process, the dwell vessel thus performs the function of an evaporator, the vapor containing the more readily volatile components in higher concentration being fed to the rectification section of the rectification column and the bottom liquid containing the more readily volatile components in lower concentration being fed to the stripping section of the rectification column. Accordingly, the dwell tank may be designed, for example, as an evaporator with self-circulation, as an evaporator with forced circulation, as a flash evaporator, as a thin-film evaporator (Sambay or Luva evaporator) or as a falling film evaporator. The dwell evaporator can of course be designed as a one-stage or multistage unit.

The residence time in the dwell vessel of the starting mixture to be separated by rectification is advantageously from 0.1 to 3 hours. In order to keep the temperatures in the rectification column as low as possible, the novel isolation of the (meth)acrylic acid by rectification is carried out very generally preferably at reduced pressure. If said isolation is effected by take-off via the top or side, a top pressure of $\leq 500$, usually from 10 to 500, frequently from 10 to 200, preferably from 10 to 100, mbar is advantageously employed, according to the invention; in a corresponding manner, the associated temperatures at the bottom of the rectification column are as a rule from 100° to 230° C.

Suitable rectification columns for the novel process are all conventional types, ie. the rectification column may be, for example, a tray-type column or a packed column. Tray-type columns are preferably used. Examples are valve tray columns, bubble tray columns, tunnel-cap tray columns, sieve plate columns and dual flow plate columns. Bubble trays are preferably used. The separation line between rectification section and stripping section of the rectification column is advantageously roughly at the end of the first third of the zone between the lowermost and the uppermost theoretical plates.

The novel procedure described above is the result of extensive research work, during which the following relationships were found. First, it was found that resin formation attributable to the aldehydic impurities is involved in particular in the formation of coatings in the stripping section of the rectification column (in particular on the evaporator surface), owing to the elevated temperatures prevailing there. As a result of the starting mixture to be separated by rectification being fed, according to the invention, to the rectification column, the relatively readily volatile part of the aldehydic impurities passes via the vapor-side connection of the dwell tank to the rectification section of the rectification column directly into said rectification section, which prevents participation of these aldehydic impurities in resin formation in the stripping section and thus reduces said formation. Another part of the aldehydic impurities is converted into resinous form in the dwell evaporator itself. It has also been found that, in spite of the starting mixture to be separated by rectification being stabilized by means of usual amounts of conventional polymerization inhibitors, a certain degree of free radical oligomerization and/or polymerization of the (meth)acrylic acid takes place in said mixture before it is fed into the rectification column. However, the resulting (meth)acrylic acid oligomers and/or polymers have, as a rule, sufficient molecular and/or colloidal solubility in the starting mixture to be separated by rectification, and are therefore not usually visible before said mixture is fed into the rectification column. Owing to their high boiling point, these (meth)acrylic acid oligomers and/or polymers accumulate within the rectification column, but toward the evaporator, and, on exceeding their solubility, are deposited as a coating on the rectification apparatuses and are firmly adsorbed onto said apparatuses. The latter applies in particular to the evaporator surface, on which the solubility limit is particularly readily exceeded owing to evaporation. As a result of the use, according to the invention, of a dwell evaporator stage upstream of the rectification column, a part of the (meth)acrylic acid oligomers and/or polymers contained in solubilized form in the starting mixture to be separated by rectification is for various reasons separated off as early as the dwell evaporator stage, increasing the operating time of the actual rectification apparatus (what is important here is that the boiling point in the upstream dwell evaporator stage is below the temperature at the bottom of the rectification column).

The latter applies in particular when the rectification process relates to the isolation of (meth)acrylic acid from a mixture containing (meth)acrylic acid and an inert hydrophobic organic liquid having a higher boiling point than (meth)acrylic acid, as main components, and lower aldehydes as secondary components, as occurs, for example, in the isolation of (meth)acrylic acid from the reaction gas mixture of the catalytic gas-phase oxidation by the procedures described in DE-A 4 436 243, German Patent 2,136,396 and DE-A 4 308 087, ie. when the starting mixture intended for the novel process and containing (meth)acrylic acid and an inert hydrophobic organic liquid having a boiling point higher than (meth)acrylic acid, as main components, and lower aldehydes as secondary components was obtained, for example from the reaction gas mixtures of the catalytic gas-phase oxidation, as a liquid discharge of a countercurrent absorption with subsequent desorption by stripping according to German Patent 2,136,396 or DE-A 4 308 087, or as a liquid discharge of a countercurrent absorption with superposed rectification according to DE-A 4 436 243. Here, high-boiling inert hydrophobic organic liquid is to be understood as meaning those liquids whose boiling point at atmospheric pressure (1 atm) is above the boiling point of (meth)acrylic acid and in which the solubility (% by weight, based on the weight of the solution) of (meth)acrylic acid oligomers and/or polymers at 25° C. and 1 atm is lower than that in pure (meth)acrylic acid.

In particular, there are those high-boiling organic liquids which comprise at least 70% by weight of those molecules which contain no externally acting polar groups and, for example, are therefore incapable of forming hydrogen bridges. In a narrower sense, the definition in this case includes the high-boiling organic absorption liquids which are recommended in German Patent 2,136,396, DE-A 4 308 087 and DE-A 4 436 243. These are essentially liquids whose boiling point at atmospheric pressure is above 160° C. Examples are middle oil fractions from paraffin distillation, diphenyl ether, biphenyl or mixtures of the abovementioned liquids, for example a mixture of from 70 to 75% by weight of diphenyl ether and from 25 to 30% by weight of biphenyl. Another advantageous high-boiling hydrophobic organic absorption liquid is a mixture comprising a mixture of from 70 to 75% by weight of diphenyl ether and from 25 to 30% by weight of biphenyl, and, based on this mixture, from 0.1 to 25% by weight of o-dimethyl phthalate.

In the case of methacrylic acid, the preparation by gas-phase catalytic oxidation may have been effected, for example, starting from methacrolein, which in turn may have been obtained by gas-phase catalytic oxidation of tert-butanol, isobutane or isobutene or by reaction of formaldehyde with propionaldehyde according to EP-B 92 097 or EP-B 58 927. Frequently, the gas-phase catalytic oxidation of tert-butanol, isobutane or isobutene is carried out using a catalytically active material of the general formula I $$Mo_{12}Bi_aFe_bX^1_cX^2_dX^3_eX^4_fO_n \qquad (I)$$

where $X^1$ is nickel and/or cobalt, $X^2$ is thallium, an alkali metal and/or an alkaline earth metal, $X^3$ is phosphorus, arsenic, boron, antimony, tin, cerium, lead, niobium and/or tungsten, $X^4$ is silicon, aluminum, titanium and/or zirconium, a is from 0.5 to 5, b is from 0.01 to 3, c is from 3 to 30, d is from 0.02 to 2, e is from 0 to 25, f is from 0 to 10 and n is an integer which is determined by the valency and frequency of the elements in I other than oxygen, at from 300° to 400° C. and, apart from the specific temperature curve, otherwise under the conditions of DE-A 4 023 239. The resulting methacrolein is used for the further oxidation, as a rule without intermediate purification. The gas-phase catalytic oxidation of the methacrolein can, apart from the specific temperature curve, be carried out according to DE-A 4 132 263 at from 200° to 350° C. or according to DE-A 4 132 684 at from 250° to 400° C. In particular, the multimetal oxide catalysts stated in DE-A 4 022 212 may be used.

In the case of acrylic acid, the preparation by gas-phase catalytic oxidation may have been carried out, for example, in one stage starting from acrolein or in two stages starting from propylene via acrolein.

Suitable multimetal oxide catalysts of the catalytic gas-phase oxidation of propylene are in particular those of the general formula II $$Mo_{12}Bi_aFe_bX^1_cX^2_dX^3_eX^4_fO_n \qquad (II)$$

where $X^1$ is nickel and/or cobalt, $X^2$ is thallium, an alkali metal and/or an alkaline earth metal, $X^3$ is phosphorus, arsenic, boron, antimony, tin, cerium, lead, niobium and/or tungsten, $X^4$ is silicon, aluminum, titanium and/or zirconium, a is from 0.5 to 5, b is from 0.01 to 3, c is from 3 to 10, d is from 0.02 to 2, e is from 0 to 5, f is from 0 to 10 and n is an integer which is determined by the valency and frequency of the elements other than oxygen, and suitable multimetal oxide catalysts for the catalytic gas-phase oxidation of acrolein are in particular those of the general formula III $$Mo_{12}V_aW_bCu_cNi_dX^1_eX^2_fX^3_gX^4_hX^5_iO_n \qquad (III)$$

where $X^1$ is one or more alkali metals, $X^2$ is one or more alkaline earth metals, $X^3$ is chromium, manganese, cerium and/or niobium, $X^4$ is antimony and/or bismuth, $X^5$ is silicon, aluminum, titanium and/or zirconium, a is from 1 to 6, b is from 0.2 to 4, c is from 0.5 to 6, d is from 0.2 to 6, e is from 0 to 2, f is from 0 to 3, g is from 0 to 5, h is from 0 to 40, i is from 0 to 40 and n is an integer-which is determined by the valency and frequency of the elements other than oxygen.

The reaction gases of the first oxidation stage are usually fed to the second oxidation stage without intermediate purification. The reaction conditions usually used are described, for example, in DE-A 4 431 957 and DE-A 4 431 949.

As a rule, such a mixture described above and consisting essentially of (meth)acrylic acid and an inert hydrophobic organic liquid having a higher boiling point than (meth) acrylic acid, as main components, and lower aldehydes as secondary components contains from 5 to 25, in general from 5 to 15, % by weight of (meth)acrylic acid.

Of course, the novel process is carried out in the presence of conventional amounts of the usual polymerization inhibitors. Phenothiazine is preferably used as the polymerization inhibitor. The polymerization inhibitors are usually used in amounts of from 50 to 1000 ppm, based on the weight of (meth)acrylic acid. Furthermore, owing to the inhibiting effect of atmospheric oxygen on the polymerization of (meth)acrylic acid, the rectification column is advantageously operated with air flowing through.

The novel process can of course also be used in combination with other prior art processes for suppressing the formation of coatings.

In the novel process, coatings must of course be removed from the dwell evaporator from time to time. By switching over to a second dwell evaporator, the operation of the rectification column can, however, be maintained.

EXAMPLES (The procedure was carried out in the presence of 200 ppm (based on the weight of the acrylic acid) of phenothiazine as polymerization inhibitor).

a) A reaction gas mixture containing acrylic acid was produced by catalytic gas-phase oxidation of acrolein according to Example B1 of DE-A 4 302 991. 2.1 Nm$^3$ (S.T.P.)/l of this reaction gas mixture were cooled to 170° C. in a gas cooler by spraying in a coolant mixture comprising 57.4% by weight of diphenyl ether, 20.7% by weight of biphenyl and 20% by weight of o-dimethyl phthalate.

The portion of the coolant which had remained liquid was then separated, in a separator, from the gas phase consisting of reaction gas and vaporized coolant. The gas phase at 170° C. was introduced, below the first tray, into a bubble tray column with 27 trays having a diameter of 80 mm and was exposed to the countercurrent of 3 l/h of the absorbent which likewise comprised 57.4% by weight of diphenyl ether, 20.7% by weight of biphenyl and 20% by weight of o-dimethyl phthalate and was added at the top of the column at 45° C. The discharge of the absorption column was heated indirectly to 105° C. in a heat exchanger and added to the top of a desorption column which was in the form of a bubble tray column having 20 trays. In the desorption column, components which are low-boiling compared with acrylic acid, such as acetic acid, were substantially removed from the mixture otherwise containing acrylic acid/lower aldehydes/absorbent by stripping with nitrogen (400 l/h, countercurrent). The discharge of the desorption column consisted of 84.5% by weight of absorbent, 15% by weight of acrylic acid and in particular lower aldehydes as secondary components.

It was introduced at 25° C. in an amount of 3 l/h between the fifth and sixth tray (counted from the evaporator) into a rectification column which comprised 20 bubble trays and had a diameter of 80 mm and through which air flowed. The rectification column was operated at a bottom temperature of 160° C. and a bottom pressure of 130 mbar and at a top pressure of 80 mbar.

60 ml of acrylic acid in a purity of 99.3% by weight were taken off continuously per hour in a side stream between the fifteenth and sixteenth tray (counted from the evaporator). The top product in the form of vapor was condensed, polymerization inhibitor was added and, apart from a take-off stream of 5 ml/h, the mixture was recycled to the rectification column, above the uppermost bubble tray.

After an operating time of 165 hours, it was necessary to stop the operation of the rectification column owing to pronounced formation of coating in the stripping section of the rectification column.

b) As in the case of a), except that the discharge of the desorption column was first fed into a heatable round-bottomed flask having a capacity of 500 ml, heated to 150° C. in said flask and, with a residence time of 0.5 h and a working volume of 250 ml, was fed via a lower discharge of the round-bottomed flask to the rectification column, between the fifth and sixth tray (counted from the evaporator). After an operating time of 167 hours, it was necessary to stop the operation of the rectification column. Essentially no formation of coating was detectable on the inner surface of the round-bottomed flask serving as a dwell tank.

c) As in the case of b), except that the round-bottomed flask serving as a dwell tank was connected via a vapor tube to the rectification section of the rectification column, directly above the lowermost bubble tray of the rectification section. The operating time of the rectification column until shutdown was required increased to 276 hours. Formation of coating occurred on the inner surface of the round-bottomed flask serving as a dwell tank.

We claim:

1. A process for the isolation of (meth)acrylic acid, comprising:

providing a mixture comprising (meth)acrylic acid as a main component and lower aldehydes as secondary components;

feeding the mixture into a heated dwell vessel connected to a column, wherein the mixture in the heated dwell vessel forms a bottom liquid and a vapor, wherein the column consists of a stripping section and a rectification section;

boiling the mixture in the heated dwell vessel such that the vapor formed passes from the heated dwell vessel into the rectification section and the bottom liquid in the dwell vessel passes from the heated dwell vessel into an entry point in the column which entry point is at an intersection of the stripping section and the rectification section, with the stripping section being below the entry point and the rectification section being above the entry point;

isolating the (meth)acrylic acid from the column, wherein the heated dwell vessel is maintained at a temperature lower than a temperature in a bottom portion of the column.

2. The process as claimed in claim 1, wherein the vapor from the heated dwell vessel comprises lower aldehydes of the mixture and the bottom liquid from the heated dwell vessel comprises (meth)acrylic acid.

3. The process as claimed in claim 1, wherein the (meth) acrylic acid is isolated from the rectification section of the column.

4. The process as claimed in claim 1, wherein the mixture has a residence time in the dwell vessel of from 0.1 to 3 hours.

5. The process as claimed in claim 1, wherein the temperature in the bottom portion of the column is from 100° to 230° C.

6. The process as claimed in claim 1, wherein said isolating step is performed in the column at a reduced pressure of from 10 to 500 mbar.

7. A process for the isolation of (meth)acrylic acid, comprising:

providing a mixture comprising (meth)acrylic acid as a main component and lower aldehydes as secondary components;

feeding the mixture into a heated dwell vessel connected to a column, wherein the mixture in the heated dwell vessel forms a bottom liquid and a vapor, wherein the column consists of a stripping section and a rectification section;

boiling the mixture in the heated dwell vessel such that the vapor formed passes from the heated dwell vessel into the vapor side of the rectification section and the bottom liquid in the dwell vessel passes from the heated dwell vessel into an entry point in the column, which entry point is at an intersection of the stripping section and the rectification section, with the stripping section being below the entry point and the rectification section being above the entry point, wherein the vapor from the heated dwell vessel comprises lower aldehydes from the mixture and the bottom liquid from the heated dwell vessel comprises(meth)acrylic acid from the mixture, and wherein the mixture has a residence time in the heated dwell vessel of from 0.1 to 3 hours and the heated dwell vessel is maintained at a temperature lower than a temperature in a bottom portion of the column; and isolating the (meth)acrylic acid from the column.

* * * * *